United States Patent [19]

Davis

[11] Patent Number: 5,713,877
[45] Date of Patent: Feb. 3, 1998

[54] INDWELLING MAGNETICALLY-ACTUATED URINARY CATHETER, AND METHOD OF ITS CONSTRUCTION

[75] Inventor: Richard C. Davis, Tampa, Fla.

[73] Assignee: Urocath Corporation, Tampa, Fla.

[21] Appl. No.: 658,568

[22] Filed: Jun. 5, 1996

[51] Int. Cl.[6] .................................................. A61M 5/00
[52] U.S. Cl. .......................... 604/246; 128/DIG. 25; 600/29; 251/65
[58] Field of Search ................... 604/8, 9, 65, 96, 604/246, 247, 280, 327, 328; 128/DIG. 25; 600/12, 29, 30, 31; 251/65, 129.21, 337

[56] References Cited

U.S. PATENT DOCUMENTS

| | | |
|---|---|---|
| 3,503,400 | 3/1970 | Osthagen et al. ............ 128/DIG. 25 |
| 3,812,841 | 5/1974 | Isaacson ........................ 251/65 |
| 3,865,666 | 2/1975 | Shoney . |
| 3,901,965 | 8/1975 | Honeymann, III . |
| 3,959,429 | 5/1976 | Benning . |
| 4,005,166 | 1/1977 | Quick . |
| 4,210,478 | 7/1980 | Shoney . |
| 4,284,459 | 8/1981 | Patel et al. . |
| 4,344,435 | 8/1982 | Aubin ............................ 604/246 |
| 4,350,161 | 9/1982 | Davis, Jr. . |
| 4,551,292 | 11/1985 | Fletcher et al. . |
| 4,723,946 | 2/1988 | Kay . |
| 4,784,651 | 11/1988 | Hickey . |
| 4,898,702 | 2/1990 | Elkins et al. . |
| 4,932,938 | 6/1990 | Goldberg et al. . |
| 5,004,454 | 4/1991 | Beyar et al. ................... 251/65 |
| 5,041,092 | 8/1991 | Barwick . |
| 5,112,306 | 5/1992 | Burton et al. . |
| 5,135,599 | 8/1992 | Martin et al. . |

*Primary Examiner*—Michael Powell Buiz
*Assistant Examiner*—Bishma Mehta
*Attorney, Agent, or Firm*—Griffin, Butler, Whisenhunt & Kurtossy

[57] ABSTRACT

An indwelling magnetically actuable urinary catheter (35) involves the molding of a valve housing (32) to a catheter drainage shaft (16) by using a drainage-valve-cavity mandrel (22) and two inflation-valve-cavity mandrels (24). The drainage-valve-cavity mandrel (22) forms a spring seat having a built in integral bypass and a valve seat. An elongated one-piece valve popper (50) of Ferro-magnetic material has an enlarged, rounded, bulbous head facing the valve seat and an elongated smaller diameter portion directed toward the spring seat for engaging the tapered spring supported by the spring seat.

19 Claims, 2 Drawing Sheets

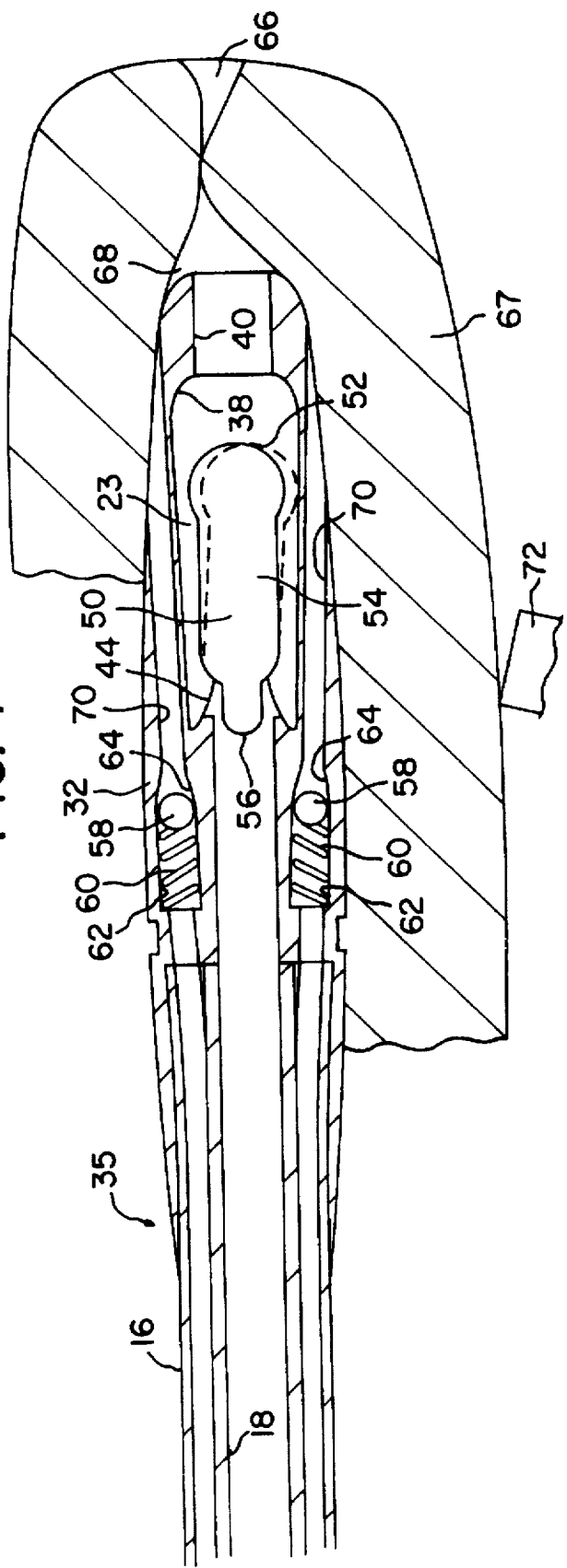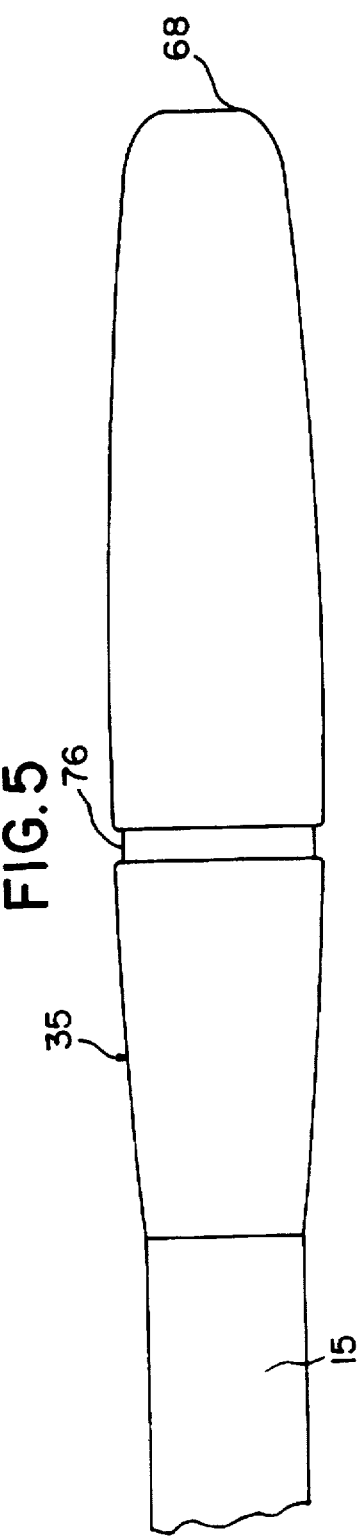

INDWELLING MAGNETICALLY-ACTUATED URINARY CATHETER, AND METHOD OF ITS CONSTRUCTION

BACKGROUND OF THE INVENTION

This invention relates to urethral catheters and more specifically, to male indwelling urethral catheters which do not extend externally out of patients while allowing the patients to urinate using external magnetic actuators.

Indwelling urethral catheters of the general type to which this invention relates were first disclosed in U.S. Pat. No. 4,350,161 Richard C. Davis, Jr. A common feature of such catheters is a valve, which, when the catheter is properly anchored in a patient's urethra, is positioned in the patient's penile urethra and can be actuated by application of a force external to the penis. U.S. Pat. No. 5,041,092 to Barwick discloses such a urethral indwelling catheter employing a magnetically actuable drainage valve in which the valve is located in the patient's pendulous penis and is actuated by the patient placing a magnetic field external to the pendulous penis proximate the magnetically-actuated valve. The valve described in Barwick, although functional, has several problems. One problem is that its housing and poppet assembly are constructed of an unduly large number of parts. Because of this, this valve is expensive and difficult to manufacture and to integrate into a catheter.

Similarly, because of the large number of parts, the valve described in Barwick (U.S. Pat. No. 5,041,092) requires an undue number of manufacturing steps to produce.

Yet other difficulties with the Barwick valve are that it has not been as reliable as would be desired and it has not been as easy to actuate as would be desired. Further, flow rates achieved with the Barwick valve have not been as great as is desired.

Thus, it is an object of this invention to provide an indwelling, magnetically-actuated urinary catheter having a magnetically-actuated valve assembly which has relatively few parts and which can be constructed relatively easily and inexpensively.

Similarly, it is an object of this invention to provide a method of constructing a magnetically-actuated valve assembly for an indwelling magnetically-actuated urinary catheter which is relatively easy to actuate and which involves relatively few steps to fabricate, insert and remove.

It is also an object of this invention to provide a magnetically-actuatable valve assembly for an indwelling urinary catheter (as well as a method of its manufacture) which is reliable in operation and which can be relatively easily actuated.

It is yet a further object of this invention to provide a magnetically-actuated valve assembly (and a method of its manufacture) which can be relatively easily integrated into an indwelling urethral catheter without adversely affecting flow of urine through the catheter.

It is also an object of this invention to provide a magnetically-actuated valve assembly which is not easily subject to blockage, but if a blockage should occur, can be easily irrigated to remove the blockage.

SUMMARY OF THE INVENTION

According to principles of this invention, an indwelling magnetically-actuated urinary catheter and a method of its construction involve a valve housing which is molded directly onto a catheter drainage shaft. In this regard, upstream ends of a drainage-valve-cavity mandrel and inflation-valve-cavity mandrels, are respectively inserted into a drainage lumen and inflation lumens of the catheter drainage shaft, with downstream ends of the mandrels being held in a jig or mold base. The mandrels are surrounded by a valve-housing mold into which a material is placed for forming a valve housing. The mold and mandrels are removable so that the valve housing is left permanently bonded to and integral with the catheter drainage shaft.

In a preferred embodiment, there are two inflation mandrels which converge inwardly away from the jig or mold base. The valve housing is molded to form a non-symmetrical spring seat with a plurality of bypass passages about a spring seated on the spring seat. The spring has a conical shape with a base thereof resting on the spring seat. The spring seat has spring seat lips for retaining the spring base on the spring seat.

An elongated drainage poppet is formed of one piece having an enlarged bulbous rounded valve head at a downstream end, a reduced intermediate portion attached to the valve head, and a diminished spring engaging tip attached to the intermediate portion at an upstream end. The valve head cooperates with a rounded valve seat molded in a drainage-valve cavity of the valve housing by the drainage-valve-cavity housing.

BRIEF DESCRIPTION OF THE DRAWINGS

This invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIG. 4 is a view similar to FIG. 2, but being rotated 90° therefrom about an axis of elongation, and including a penis and external magnet actuator, thus showing compression of a conical spring; and FIG. 5 is a view similar to FIGS. 2 and 4, but the catheter is shown in elevational view rather than cross section.

DESCRIPTION OF THE PREFERRED EMBODIMENT

Figure 1:
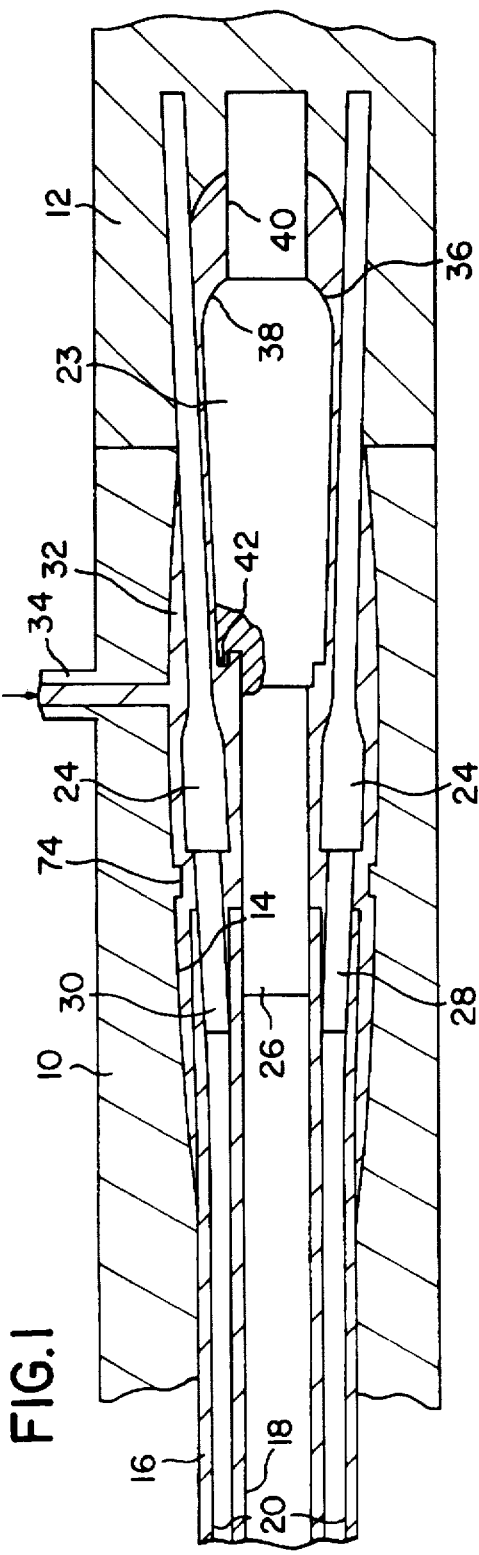
FIG. 1 is a schematic axial cross sectional view of a mold for molding a valve housing of this invention along with a drainage-valve-cavity mandrel, two inflation-valve-cavity mandrels, a jig (or mold base) holding the mandrels and a catheter drainage shaft.

FIG. 1 depicts a step in a process of this invention for manufacturing an indwelling magnetically-actuated urinary catheter of this invention in which a mold 10 and a jig 12 or mold base are used. It will be understood by those of ordinary skill in the art that molds and jigs can have various forms and the mold and jig depicted in FIG. 10 are shown in a schematic manner for purposes of simplicity.

The mold 10 defines an elongated, circular-in-cross section, mold cavity 14 in which is inserted from an upstream end (upstream being oriented in a direction pointing toward a patient's bladder - - - the left in FIG. 1) a catheter drainage shaft 16 which was previously prepared. The catheter drainage shaft 16 defines a central large drainage lumen 18 and two smaller, off-center, oppositely-positioned inflation lumens 20. The drainage lumen 18 allows urine to flow downstream away from the bladder while the inflation lumens 20 provide fluid paths for inflating and deflating anchoring balloons (not shown). The catheter drainage shaft 16 is held in the upstream end of the mold 10 while a drainage-valve-cavity mandrel 22 and two inflation-valve-cavity mandrels 24 are held in the mold cavity 14 from a downstream end by the jig 12. In this regard, the jig 12 is connected or affixed to the drainage-valve-cavity mandrel 22 and the inflation-valve-cavity mandrels 24 so that it can be used for manipulating these mandrels relative to the mold cavity 14. The jig 12 can also be used for closing the downstream end of the mold 10. In the schematic embodiment depicted in FIG. 1, the jig 12 actually also forms an extension of the mold cavity 14.

In a preferred embodiment, the inflation-valve-cavity mandrels 24 are held at inwardly converging angles in the mold cavity 14; alternately they may be held straight but constructed of a flexible material allowing them to be urged inwardly upon insertion into the inflation lumens 20 of the catheter drainage shaft 16.

Lumen-forming ends 26, 28 and 30 of the drainage-valve-cavity mandrel 22 and the inflation-valve-cavity-mandrels 24 are respectively inserted into downstream ends of the drainage lumen 18 and the inflation lumens 20. The mold 10 is then closed over the three mandrels 22 and 24 and the catheter drainage shaft 16.

For purposes of simplicity, the manner in which the mold 10 is closed and released is not depicted in FIG. 1.

It should be understood that the jig 12 may also be designed in such a fashion that would allow either simultaneous or independent relative movement of the 3 mandrels attached thereto.

Figure 2:
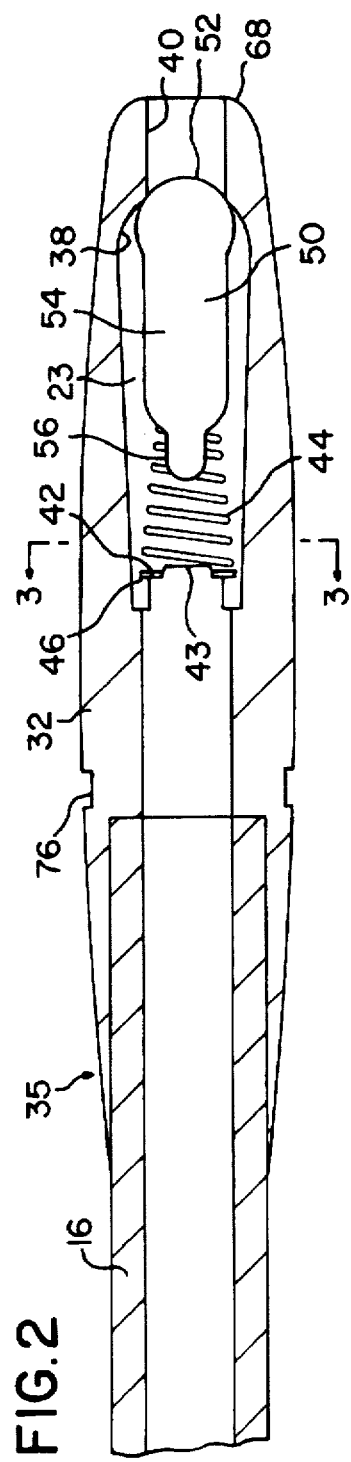
FIG. 2 is an axial cross sectional view of a downstream end of an indwelling magnetically-actuated urinary catheter of this invention of a type having a valve housing constructed using the step illustrated in FIG. 1.

A valve housing 32 (FIG. 2) of this invention is constructed in one step by setting up the mold and mandrels as depicted in FIG. 1 and described above and injecting a medical-grade silicone rubber into a nipple 34 of the mold 12 to fill the mold cavity 14. It will be appreciated by those of ordinary skill in the art that the mold 10 is a standard LIM (Liquid Injection Mold) compression mold which forms an exterior shape of the valve housing 32 while the drainage-valve-cavity mandrel 22 and the inflation-valve-cavity mandrels 24 form interior shapes of the valve housing 32; the drainage-valve-cavity mandrel 22 forming a drainage-valve cavity 23 and integral spring seat 42 and the inflation-valve cavity mandrels 24 forming inflation-valve cavities 62 (FIG. 4). Since the catheter drainage shaft 16 is also constructed of a medical grade silicone rubber, the molding step described above fuses the valve housing 32 to the catheter drainage shaft 16, with lumens formed by the lumen-forming ends 26, 28 and 30 of the mandrels 22 and 24 communicating with the drainage lumen 18 and the inflation lumens 20 of the catheter drainage shaft 16.

Once the valve housing 32 has sufficiently hardened, the mold 10 is opened and the jig 12 is retracted to the right (in the downstream direction), along with mandrels 22 and 24, either simultaneously or independently. Thus, the valve housing 32, fused to the catheter drainage shaft 16, is produced. Alternately, with the mold open, the now fused valve housing 32, being sufficiently flexible, may simply be pulled off the three mandrels 22 and 24 with axial traction applied from the upstream direction.

Figure 3:
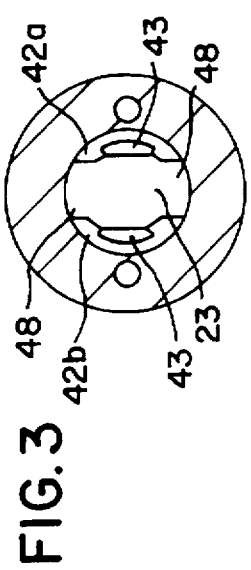
FIG. 3 is a cross sectional view taken on line III—III in FIG. 2.

As can be seen in FIG. 1, the drainage-valve-cavity mandrel 22 has a rounded shape 36 at a downstream end of the urethral valve cavity 23 so as to form a rounded drainage valve seat 38 surrounding an outlet port 40. The outlet port 40 has at least as great a cross-sectional area as does the drainage lumen 18. The spring seat 42 is molded, by the drainage-valve-cavity mandrel 22, at an upstream end of the urethral valve cavity 23 for supporting a conical, or tapered, compression coiled spring 44, whose base 46 rests on the spring seat 42. The drainage-valve-cavity mandrel 22 is especially shaped to mold this unusual spring seat 42 as one piece with the valve housing 32. In this regard, it can be seen in FIG. 3 that the spring seat 42 is divided into two parts 42a, 42b located on opposites sides of the drainage-valve cavity 23. Between the two parts 42a, 42b of the spring seat 42 there are two passages 48 which allow urine to flow around the outside of the tapered compression coiled spring 44. Another feature of the spring seat 42 is that each of the opposite sides of the seat has an axially-directed molded lip 43 for retaining the base 46 of the tapered compression coiled spring 44 on the spring seat 42.

An elongated drainage-valve poppet, or rod, 50 is inserted into the drainage-valve cavity 23. The elongated drainage-valve popper 50 has an enlarged, bulbous, rounded valve head 52 directed downstream to come into contact with the drainage valve seat 38, a smaller-diameter elongated, axially-oriented intermediate portion 54 and a smaller-yet spring-engaging tip 56 to engage in an apex end of the tapered compression coiled spring 44. Thus, the tapered compression coiled spring 44 presses against the spring seat 42 to drive the valve head 52 of the drainage-valve poppet 50 in a downstream direction against the drainage valve seat 38.

The drainage-valve poppet 50 can be constructed of ferromagnetic materials coated with gold or other non-corroding material so as to be attracted to an external magnetic source, thus allowing deflection and valve actuation thereby.

On the other hand, the tapered compression coiled spring 44 is formed of a non-magnetic material such as non ferrous stainless steel alloys or any other suitable non-magnetic spring material. Alternately, in another configuration the spring material may be of suitable ferromagnetic material. Alternately, the spring may be molded as a one-piece integral portion with the seat.

The drainage-valve popper, or rod, 50 thusly has this special shape, with its valve head 52 defining an arc in an axial plane of about 270° and having a radius in a plane perpendicular to the axis of elongation substantially greater than a radius of the outlet port 40. This structure allows the valve head 52 to remain in sealing contact with the valve seat 38 even if the entire drainage-valve popper 50 is at a 60° angle relative to the axis of elongation of the valve housing 32. Since the valve housing 32 is constructed of silicone rubber and is very flexible, and since the housing is mounted in a flexible penis, the valve is designed to remain closed even in conditions of severe axial deformation or bending. Thus, the bulbous shape of the valve head 52, in combination with the elongated intermediate portion 54, allows the drainage-valve poppet 50 to seat in virtually all possible anatomic attitudes that the penis experiences.

Turning to FIG. 4, spherical inflation valves 58 and inflation compression springs 60 are inserted into the inflation-valve cavities 62 formed by the inflation-valve-cavity mandrels 24. The inflation springs 60 drive the spherical inflation valves 58 in a downstream direction toward restrictive inflation valve seats 64 which are formed in the inflation-valve cavities 62.

To use the indwelling magnetically-actuated urinary catheter 35, an upstream tip, not shown, of the indwelling magnetically-actuated urinary catheter 35, having a bladder balloon and a urethral cuff balloon attached thereon (not shown), is inserted into a meatus 66 of a penis 67 until the bladder balloon is positioned in the bladder. In this configuration, a downstream end 68 of the indwelling magnetically-actuated urinary catheter 35, is attached to an inflation/drainage member (not shown) having pins frangibly inserted into inflation lumens 70 and into the outlet port 40 for respectively holding the inflation valves 58 and the drainage-valve poppet 50 away from their respective valve seats 64, 38. Fluid is inserted into the inflation lumens 70 to inflate the bladder balloon and the urethral cuff. Once the indwelling magnetically-actuated urinary catheter has been thusly anchored, with its downstream end 68 inwardly spaced from the penile meatus 66, the inflation/drainage member (not shown) is removed, thereby allowing the inflation valves 58 and the drainage-valve poppet 50 to close and seal on their respective valve seats 64, 38.

When the patient desires to urinate, he places an external magnetic source 72 (FIG. 4) adjacent, but slightly upstream, of the drainage-valve poppet 50. When he does this, the drainage-valve poppet 50 is pulled away from the drainage valve seat 38; thus, compressing the tapered compression coiled spring 44 so that urine can drain through the outlet port 40 and the penile meatus 66. Once the patient has urinated, he removes the external magnetic source 72 and the tapered compression coiled spring 44 drives the head 52 of the drainage-valve poppet into sealing contact with the drainage valve seat 38, even if the drainage-valve poppet 50 is at an angle, as depicted in the dashed lines in FIG. 4, and even if the entire valve is deformed or bent at severe angles of up to 60°.

The mold 10 (FIG. 1) has an annular protrusion 74 thereon for creating an indentation ring 76 in the valve housing 32 immediately upstream of the inflation-valve for indicating a location at which a user may cut the valve housing 32 in order to quickly and easily (in one step) deflate the bladder balloon and urethral cuff balloon for removing the catheter. A dyed band can be placed in this indentation ring 76 in order to make it more visible, as well as to make the overall surface of the valve smooth.

It is advantageous that the spring seat 42, which is integral with the valve housing 32, is divided into two parts so that passage openings 48 between these two parts 42a and 42b allow urine to freely flow through and past the spring seat 42 and the tapered compressed coil spring 44. In fact, the spring seat 42 and the spring 44 are constructed such that they provide a greater flow area than does the drainage lumen 18 of the catheter drainage shaft 16.

With regard to construction of the spring it is a quite beneficial feature that the compression coiled spring 44 is tapered inwardly away from the spring seat 42. By making the spring in a tapered, conical, design, the spring does not cut off urine flow through its coils as it is compressed. That is, the coils of the spring do not seat against one another to close the opening in the middle of the spring seat 42. This tapered design also resists kinking and thus reduces binding of the spring with interior walls forming the valve cavity 23, while also tending to center the spring engaging tip 56.

It is also beneficial that the integral spring seat 42 includes an integral spring-seat lip 43 for centrally retaining the spring 44 on the spring seat 42.

It is extremely helpful that the valve housing 32, including the valve cavity 23, the inflation-valve cavities 62, the spring seat 42, the drainage valve seat 38, and the inflation valve seats 64, are all molded as one integral part. This simplifies construction of the indwelling magnetically-actuated urinary catheter of this invention tremendously. In this regard, such a construction method reduces the number of parts and steps required for the catheter's manufacture, thus reducing costs and increasing reliability.

It is also quite helpful that the drainage-valve popper 50 is shaped as an elongated rod, with a bulbous valve head 52 at a seating end thereof because this allows it to seat against the drainage valve seat 38 even if the drainage-valve popper 50 is at an extreme angle relative to the axis of elongation of the valve housing 32. Further, by making the drainage valve popper 50 to have a relatively long intermediate portion 54, it is assured that the bulbous valve head 52 remains oriented so that it can properly seat on the drainage valve seat 38. Finally, by including a spring-engaging tip 56 on the drainage-valve popper 50, it is assured that the drainage-valve poppet 50 maintains engagement with the apex of the tapered compression coiled spring 44. In one embodiment, the spring-engaging tip 56 actually has threads on it so that it can threadingly engage with the apex of the tapered compression coil spring 44.

It is also quite helpful that the elongated valve cavity, the compression spring and the value rod provide at least as great a cross-sectional flow area through the valve housing when the valve head is pulled fully away from the valve seat as does the drainage lumen of the urethral shaft. This structure ensures that the valve does not impede flow or become clogged.

By placing a prominent mark or band on the valve housing 32 immediately upstream of the inflation valves 58, the user is guided to cut the indwelling magnetically-actuated urinary catheter 35 at the most accessible location for deflating the bladder balloon and the urethral cuff for quickly removing the indwelling magnetically-actuated urinary catheter.

While the invention has been particularly shown and described with reference to a preferred embodiment, it will be understood by those skilled in the art of various changes in form and detail may be made therein without departing from the spirit and scope of the invention.

For example, it is obvious to those skilled in the art that the drainage poppet's orientation and that of the rounded valve seat may be reversed 180° in certain other desirable configurations.

Further, the rod or poppet itself could be constructed of a magnet, which would allow it to be activated from greater distances.

It should be understood by those of ordinary skill in the art that the external magnet could be either a permanent magnet or an electromagnet.

Also, the valve need not be located in the pendulous penis, but could reside at some greater distance from the meatus.

The invention claimed is:

1. An indwelling magnetically-actuated urinary catheter comprising:
   a catheter drainage shaft defining a drainage lumen for draining urine from a bladder positioned at an upstream end of the catheter drainage shaft and at least one inflation lumen for inflating a positioning balloon along said catheter drainage shaft for anchoring said catheter drainage shaft;

a valve housing constructed as one piece and being integrally fused to said catheter drainage shaft for defining an elongated valve cavity communicating with the drainage lumen, said valve cavity defining a valve seat at a first end of said valve cavity and a spring seat at an opposite end of said valve cavity;

a valve rod comprised of ferromagnetic material having a valve head facing the valve seat, and an elongated smaller diameter portion directed toward the spring seat, wherein said valve rod is formed of a one-piece elongated member, with the valve head being an enlarged, rounded bulbous valve head positioned at one end of the valve rod, directed toward the valve seat for closing against said valve seat even if the valve rod is at an angle relative to an axis of elongation of the valve housing; and a compression spring situated between the spring seat and the valve rod for engaging the valve rod at an end portion of said elongated smaller diameter portion directed toward said spring seat and driving the valve head toward the valve seat.

2. An indwelling magnetically-actuated urinary catheter in claim 1 wherein the valve seat is at a downstream end of the valve cavity and the spring seat is at an upstream end of the valve cavity.

3. An indwelling magnetic-actuated urinary catheter as in claim 2 wherein said compression spring is a coil spring and said spring seat defines a passage coaxial with said elongated valve cavity for allowing urine flow into an interior of said coil spring, two ledges positioned on opposite sides of said passage for engaging said compression spring on opposite sides and bypass openings on opposite sides of said passage for allowing urine to flow around said spring.

4. An indwelling magnetically-actuated urinary catheter as in claim 3 wherein the compression spring has a conical shape.

5. An indwelling magnetically-actuated urinary catheter as in claim 4 wherein the compression spring is molded integrally as one piece with the valve housing.

6. An indwelling magnetic-actuated urinary catheter as in claim 1 wherein said compression spring is a coil spring and said spring seat defines a passage coaxial with said elongated valve cavity for allowing urine flow into an interior of said coil spring, two ledges positioned on opposite sides of said passage for engaging said compression spring on opposite sides and bypass openings on opposite sides of said passage for allowing urine to flow around said spring.

7. An indwelling magnetically-actuated urinary catheter as in claim 6 wherein the spring has a conical shape.

8. An indwelling magnetically-actuated urinary catheter as in claim 6 wherein the compression spring is molded as one piece with the valve housing.

9. An indwelling magnetically-actuated urinary catheter as in claim 1 wherein said smaller diameter portion of said valve rod has a smaller yet spring-engaging tip facing away from the valve seat toward the spring seat for engaging said compression spring.

10. An indwelling magnetically-actuated urinary catheter as in claim 9 wherein said spring has a conical shape with its apex engaging the smaller spring-engaging tip of the valve rod.

11. An indwelling magnetic-actuated urinary catheter as in claim 9 wherein said compression spring is a coil spring and said spring seat defines a passage coaxial with said elongated valve cavity for allowing urine flow into an interior of said coil spring, two ledges positioned on opposite sides of said passage for engaging said compression spring on opposite sides and bypass openings on opposite sides of said passage for allowing urine to flow around said spring.

12. An indwelling magnetically-actuated urinary catheter as in claim 1 wherein the spring has a conical shape.

13. An indwelling magnetic-actuated urinary catheter as in claim 1 wherein is further included a marker molded on said valve housing to indicate a cutting position on said valve housing at which the valve housing can be cut to relieve pressure in a positioning balloon.

14. An indwelling magnetic-actuated urinary catheter as in claim 1 wherein said elongated valve cavity, said compression spring, and said valve rod provide at least as great a cross-sectional flow area through said valve housing when said valve head is pulled fully away from said valve seat as does said drainage lumen of said catheter drainage shaft.

15. An indwelling magnetic-actuated urinary catheter comprising:

a catheter drainage shaft defining a drainage lumen for draining urine from a bladder positioned at an upstream end of the catheter drainage shaft and at least one inflation lumen for inflating a balloon in the bladder for anchoring said catheter drainage shaft;

a valve housing attached to said catheter drainage shaft for defining an elongated valve cavity communicating with the drainage lumen, said valve cavity defining a valve cavity seat at a first end of said valve and a spring seat at an opposite end of said valve cavity;

a one-piece elongated valve popper of ferromagnetic material having an enlarged, rounded bulbous valve head facing the valve seat, and an elongated smaller diameter portion directed toward the spring seat, wherein said valve poppet is formed as a one-piece elongated member for closing its enlarged, rounded bulbous valve head against said valve seat even if the valve rod is at an angle relative to an axis of elongation of the valve housing; and a compression spring situated between the spring seat and the valve poppet for engaging an end portion of the smaller diameter portion directed toward said spring seat and driving the bulbous head toward the valve seat.

16. An indwelling magnetically-actuated urinary catheter as in claim 15 wherein the compression spring has a conical shape.

17. An indwelling magnetically-actuated urinary catheter as in claim 16 wherein said smaller-diameter portion of said elongated valve popper has a smaller yet spring-engaging tip facing away from the valve seat for engaging the spring at a spring apex.

18. An indwelling magnetically-actuated urinary catheter comprising:

a catheter drainage shaft defining a drainage lumen for draining urine from a bladder positioned at an upstream end of the catheter drainage shaft and at least one inflation lumen for inflating a balloon in the bladder for anchoring said catheter drainage shaft;

a valve housing attached to said catheter drainage shaft for defining an elongated valve cavity communicating with the drainage lumen, said valve cavity defining a valve seat at a first end of said valve cavity and a spring seat at an opposite end of said valve cavity;

a valve poppet having a valve head facing the valve seat, and a portion directed toward the spring seat; and a compression spring situated between the spring seat and the valve poppet for engaging the valve popper and driving it toward the valve seat;

wherein said compression spring is a coil spring and said spring seat defines a passage coaxial with said elongated valve cavity for allowing urine flow into an interior of said coil spring, two ledges positioned on opposite sides of said passage for engaging said compression spring on opposite sides and bypass openings on opposite sides of said passage for allowing urine to flow around said spring.

19. An indwelling magnetically-actuated urinary catheter as in claim 18 wherein each of said ledges includes a lip thereon extending in a direction of elongation of said valve cavity for holding said compression spring on said ledge.

* * * * *